(12) United States Patent
Reed (10) Patent No.: US 10,639,086 B2
(45) Date of Patent: *May 5, 2020

(54) MEDICAL FASTENER

(71) Applicant: RTG SCIENTIFIC, LLC, Austin, TX (US)

(72) Inventor: Gary Jack Reed, Turlock, CA (US)

(73) Assignee: RTG Scientific, LLC, Austin, TX (US)

(*) Notice: Subject to any disclaimer, the term of this patent is extended or adjusted under 35 U.S.C. 154(b) by 117 days.

This patent is subject to a terminal disclaimer.

(21) Appl. No.: 15/690,978

(22) Filed: Aug. 30, 2017

(65) Prior Publication Data

US 2017/0360490 A1 Dec. 21, 2017

Related U.S. Application Data (63) Continuation of application No. 13/573,736, filed on Oct. 3, 2012, now Pat. No. 9,782,209.

(51) Int. Cl.
*A61B 17/86* (2006.01)

(52) U.S. Cl.
CPC ........ *A61B 17/8625* (2013.01); *A61B 17/863* (2013.01); *A61B 17/8635* (2013.01); *A61B 2017/8655* (2013.01)

(58) Field of Classification Search
CPC ... A61B 17/86; A61B 17/8625; A61B 17/863; A61B 17/8635; A61B 17/8655
See application file for complete search history.

(56) References Cited

U.S. PATENT DOCUMENTS

| | | | |
|---|---|---|---|
| 1,235,626 A * | 8/1917 | Woodward | F16B 25/0078 411/421 |
| 4,978,350 A | 12/1990 | Wagenknecht | |
| 5,720,766 A | 2/1998 | Zang et al. | |
| 5,743,914 A * | 4/1998 | Skiba | A61B 17/8625 411/412 |
| 5,759,003 A * | 6/1998 | Greenway | F16B 25/0015 411/399 |
| 5,967,783 A | 10/1999 | Um | |
| 6,231,281 B1 | 5/2001 | Nishikawa | |
| 6,743,233 B1 | 6/2004 | Baldwin et al. | |
| 7,281,925 B2 | 10/2007 | Hall | |
| 2001/0049528 A1 | 12/2001 | Kubota | |
| 2002/0123752 A1 | 9/2002 | Schultheiss et al. | |
| 2004/0243129 A1 | 12/2004 | Moumene et al. | |
| 2005/0038438 A1 | 2/2005 | Anderson et al. | |
| 2005/0228388 A1 | 10/2005 | Brodke et al. | |

(Continued)

FOREIGN PATENT DOCUMENTS

| | | |
|---|---|---|
| CN | 201624762 | 11/2010 |
| EP | 1 656 899 | 5/2006 |
| JP | H1043199 | 2/1998 |

*Primary Examiner* — Nicholas W Woodall
(74) *Attorney, Agent, or Firm* — Womble Bond Dickinson (US) LLP (57) ABSTRACT

A dual-start fastener is disclosed having two threads helically wound about its shaft. The thread tooth profile (in section) constitutes substantially parallel upper and lower facets on each thread flank. A first thread has a crest diameter greater than a second thread. A distal end of the fastener includes self-tapping cutters formed on the threads which force shards of bone to advance into shallow troughs adjacent the cutters for subsequent resorption by adjacent osseous tissue.

12 Claims, 6 Drawing Sheets

(56) References Cited

U.S. PATENT DOCUMENTS

| | | |
|---|---|---|
| 2006/0106384 A1 | 5/2006 | Reber et al. |
| 2006/0106386 A1 | 5/2006 | Reber et al. |
| 2006/0106389 A1 | 5/2006 | Reber et al. |
| 2006/0193713 A1* | 8/2006 | Gerhard ................... B21K 1/44 411/387.4 |
| 2008/0249579 A1 | 10/2008 | Taylor |
| 2010/0240010 A1 | 9/2010 | Holmström |
| 2010/0247267 A1* | 9/2010 | Bianchi ................... F16B 25/00 411/387.4 |
| 2011/0255936 A1 | 10/2011 | Stager et al. |
| 2011/0288599 A1 | 11/2011 | Michielli et al. |
| 2012/0172935 A1* | 7/2012 | Willert ............... A61B 17/8625 606/309 |
| 2014/0053696 A1 | 2/2014 | Reed |

* cited by examiner

MEDICAL FASTENER

CROSS REFERENCE TO RELATED APPLICATIONS

This application is a continuation application of U.S. patent application Ser. No. 13/573,736, filed on Oct. 3, 2012, of which the entire disclosure of the prior application is hereby incorporated by reference.

FIELD OF THE INVENTION

This invention relates generally to fasteners. More specifically, this invention pertains to threaded fasteners. Most specifically, the threaded fasteners (or screws) have particular utility for embedment in unique, typically non-homogeneous materials under dynamic loading. One common example would be bone found in the orthopedic, veterinary and dental environment.

BACKGROUND OF THE INVENTION

Homogeneous material devoid of dynamic loading has been reliably fastened in the past. However, when homogeneity varies and when dynamic loading changes, confounding fastener issues arise. Skeletal scaffolding is one example of non-homogeneous structure subjected to dynamic loading.

The skeleton is comprised of osseous tissue. Compact bone is one form of osseous tissue characterized in greater density than the other osseous tissue, called cancellous bone, trabecular bone or spongy bone. The cancellous bone has a higher surface area than the compact bone but is softer, weaker and less stiff. When embedding a screw into bone having both characteristics, the holding power of the screw (e.g. pull out strength) is limited by the screw's ability to be retained in the cancellous bone, since it is the weakest component. Yet the fastener must still be designed to cut through the compact bone. Prior art buttress threads (the industry standard) cannot address the non-homogeneity of bone under dynamic loading.

One result is the prior art's failure to provide a reliable thread portion that engages the bone of the patient in a manner which retards its working loose. Bone is a remarkable structure which varies both in hardness and elasticity as a function of both age and location. Loads on the fastener must accommodate not only these constraints but also the dynamics of forces generated by the patient in daily activities. Prior art buttress threads cannot address these requirements, resulting in the fastener working loose or even pulling out.

As a consequence, the industry custom is to offer long cancellous screws having greater pitch density to increase holding. These screws typically have shafts totally or partially threaded along the length and threads of constant crest diameter along the major length (excluding the starting, distal end) and the shaft diameter equals the crest diameter. Pull out resistance is therefore limited by the volume of cancellous bone that resides between the screw teeth and its cohesion with adjacent cancellous tissue.

The buttress thread is presently the industry standard. Acme threads are sometimes used, but are merely buttress threads with the exposed sharp thread truncated at the apex. This does not cure buttress thread frailties. Unfortunately, buttress threads are suitable for use only where load forces on the fastener are applied in one direction. (Bhandari, Design of Machine Elements (2007), page 204). Where the load forces are multidirectional or not unidirectional and axial, failure can occur. One manifestation of buttress thread failure is "toggling" where the fastener works on the bone and enlarges the hole within which the fastener resides, resulting in failure.

Screw insertion time is a function of screw length and the medium's resistance to screw advancement. In an operatory, shorter procedures are believed to promulgate better results to the extent that asepsis correlates to shorter exposure by the patient to a procedure. To address this, a few patents have proposed dual start, dual thread fasteners having two differing crest diameters ("hi-low"), one for each thread. Because the industry still embraces buttress thread geometry, they have not solved the primary problems of embedment in non-homogeneous osseous tissue under multi-directional, dynamic loading. Please see exemplary U.S. Pat. Nos. 6,743,233, 5,743,914 and 5,720,766. Curiously these patented technologies have not been adopted by the industry.

BRIEF SUMMARY OF THE INVENTION

The medical fastener of the present invention provides both greater ease in insertion, resulting in lower friction, and a greater volume of cancellous bone retained adjacent the fastener. These increase pull out strength and reduce insertion time. An important corollary is that the cancellous bone adjacent the fastener does not experience elevated temperatures due to high insertion torque caused by undesirable friction. When the temperature exceeds as little as 116 degrees Fahrenheit, osteonecrosis is known to occur which compromises pull out strength and lead to total failure of the fastener.

Reduced effort during installation provides greater feedback to the surgeon enabling an improved feel and signal that the fastener is properly installed. Presently, it is not unknown for surgeons to sense high insertion torque as one signal that there has been solid purchase by the fastener and therefore the desired quality of fixation has been achieved.

This medical fastener benefits from a dual thread wherein two thread flights are intertwined helically along the shaft. Each thread has its own self tapping starting cutter which channels bone shards into at least one shallow trough integrally formed on the shaft of the fastener. Preferably plural troughs are provided having minimal depth to receive the directed shards in a thin layer. This thin deposit of bone shard thus remains available to be assimilated by adjacent bone and minimizes the shards' becoming necrotic tissue and otherwise a site for festering.

As thus far described, the two thread paths can collectively have the same overall pitch density of a conventional fastener, if desired. However, the teeth on both thread paths (when viewed in section) depart starkly from the prior art in many important aspects. For example, the upper and lower facets on each tooth are substantially parallel. In addition, the thickness of each tooth is minimal, approaching blade-like ("feeler gauge") thinness. This structure benefits from the greater strength the fastener enjoys compared to the surrounding material into which it is embedded and dramatically reduces the torque required for installation compared to the prior art.

Moreover, because the two thread paths have differing crest diameters, the dynamics of the fastener depart dramatically from the conventional buttress thread. With two differing crest diameters, the bone into which the fastener is embedded is not retained by a core of cancellous bone having a constant "plug" diameter (i.e. equal to the crest diameter of the buttress thread and shaft diameter), but rather is retained by residual bone which surrounds both the smaller diameter and the larger diameter crest diameters, resulting in a "serpentine" or "saw tooth" continuum of cancellous bone interlaced between both crest diameters.

The result is a bone "tooth" geometry which mimics a square wave; in other words, a crenelated contour or battlement which alternately intersperses merlons and crenels. This results in an appreciable increase in the volume of retained cancellous bone surrounding the fastener. This benefit will not exist in those dual start patents listed above. In addition, the bone tooth formed by the fastener of the present invention abuts against the cylindrical shaft portion between adjacent fastener teeth. This avoids prior art pressure points where bone tapers between adjacent fastener teeth.

The pitch (spacing) in a dual start, dual thread structure, in which the thread flanks have parallel upper and lower facets or flanks provide important benefits. The pitch of one thread flight is preferably at least twice the pitch of a conventional cancellous buttress fastener. Because the two thread flights are interleaved, and because of the differing crest diameters of the two flights, more volume of cancellous bone is available for retention, resulting in greater pull out strength.

Of equal and paramount importance is the symmetry of the two thread flights being 180 degrees out of phase. This means that, in section, a lesser crest diameter is substantially directly opposite a greater crest diameter everywhere along the length. Thus, loads imposed on the fastener react simultaneously to both a larger crest and a smaller crest everywhere along the thread pattern, with loads parallel to the long axis (especially when offset) reacted to by the blade-like threads opposing each other and deflecting the forces. Loads which are not parallel to the long axis of the fastener are even more efficiently diffused by the blade structure in conjunction with the smooth shaft, since pressure points are minimized.

That is, unlike a buttress thread, spaces between each thread do not form a "V" shaped focal point (or fulcrum) which heretofore defined both stress points along the osseous tissue and a locus of failure points on the fastener. Instead, the cancellous, osseous tissue sees smooth, cylindrical expanses of fastener shaft between adjacent threads. The abutment of cancellous tissue adjacent these smooth areas improve load distribution along more bone surface without "pressure" points heretofore defined by the sharp angles of prior art buttress threads. Thus, forces transverse to the long axis are similarly opposed and deflected. Having been thus informed, it should now be clear that oblique forces are similarly vectored out.

Each thread has a flank with an upper and lower facet. Unlike buttress threads, —which are triangular (sometimes truncated) flanks in section—the upper and lower facets of each of the flanks of the instant fastener are very closely spaced together and preferably substantially parallel in section, resulting in a very thin, blade-like thread. A thread angle is defined as the included angle between an adjacent upper and lower flank.

Blade-like threads (with substantially parallel upper and lower facets) result in thread angles approximating 0 degrees. (Buttress fastener thread angles are typically 60 degrees for both single and dual start threads.) Thin threads therefore also result in minimum bone excision during installation, resulting in more bone for retention and easier installation. When taken into conjunction with the dual thread/start structure, important benefits obtain.

As mentioned, dual thread/starts reduce the pitch of each thread pattern by at least one-half to maintain the same overall pitch density. However, with the dual start/thread structure, the angle of attack (lead angle) of the thread pattern is also changed by a factor of two. This also changes the "ramp angle" (i.e. the rate at which the helical thread spirals) by a factor of 2. A helix angle may be defined as the angle included by a line approximating the slope of an upper facet and an intersecting line that is transverse to the long axis of the fastener. For example, with a single thread fastener, the helix angle is typically 11 degrees in the prior art. With a dual start, dual thread design, the helix angle would instead be about 21 degrees.

Thus, imposed force vectors are resisted not only by a greater volume of cancellous bone remaining, but also are redirected and deflected at a different, less oblique angle by the flanks of the threads. Importantly, in the present invention, these forces are redirected into the adjacent and more abundant cancellous bone. In sum, the thread angle of 0 degrees retains more bone and the higher helix angle directs forces into the more abundant bone at a preferable angle.

Perhaps paradoxically, this structure, in conjunction with the self-tapping cutters, reduces the effort and time required for installation while increasing tactile feedback to the surgeon and while increasing holding power. It is well known that dual thread structures double the axial advancement of the shaft per revolution of the shaft. The same applies here, but with the cutter, the surgeon regains feel for the advancement of the fastener screw because of the confluence of features including the improved lead angle, differing crest diameters and closely spaced, thin, substantially parallel facets found on opposing flanks of the thread. In section, these facets are substantially perpendicular to the long axis of the fastener.

Dual start threads intuitively should have at least one cutter for starting and forming each thread pattern. Cutters should be deployed in pairs, spaced diametrically opposite each other for symmetric advancement. Additional cutters should also be in pairs. By contrast, in the present invention, preferably three cutters are provided for the two thread paths, but symmetrically disposed at 120 degrees about the fastener, each with its own shard trough. The first and second cutters are disposed one on each of the two flights, 120 degrees apart and they both cooperate to form the smaller crest diameter, while the third cutter finishes cutting for the larger crest diameter threads upstream from the first two.

The present invention's thread geometry minimizes insertion force by reducing heat generating friction. This allows the surgeon tactile feedback and reduces the effort required to deploy the fastener. This, in conjunction with cutters feeding shallow shard storage troughs, a centering pilot, and improved thread cutting features keep friction low, the fastener aligned and directed from wandering away from the preferred path.

The distal end of many fasteners includes a relief area (flute) designed to help cut through bone, defining a "self-tapping" fastener. A buttress thread fastener having a self-tapping feature usually comprises a flute that is straight or at least close to in-line with the axis of the screw. As a result, as the fastener is advanced, the cutting edges send the bone chip towards the head of the fastener which is into the path of the helical threads. This bone debris accumulates along the thread teeth and increases insertion torque and friction which therefore generate additional heat. The debris also makes the fastener harder to insert and provides a poor interface with the bone and the fastener.

In the present invention, the cut chips curl away from the cutting edges and are fed into the preformed trough integral with the fastener and parallel with its long axis on an outer annular periphery. That is, as the fastener advances, the flute forces the chips downward into the adjacent trough. This results in exact clearance between the fastener and the portion of the bone being formed as "bone teeth". (Bone mass which engages the threaded fastener shall be referred to as bone teeth). The interface between the bone and fastener is therefore substantially free of the cuttings and provides healthier bone tissue adjacent the fastener to prevent additional trauma to the bone. Shards in the trough adjacent the uncut bone tissue are available to be absorbed and fed thereby, resulting in a healthier, stronger interconnection.

Another problem associated with buttress style threads is that the area between threads of the fastener is the only site of anchoring in the bone, and because of the design constraints associated therewith, this site is difficult to optimize. Stated alternatively, once the pitch and crest and root diameters are chosen, the thread pattern is fixed. Because the metal of the fastener is orders of magnitude stronger than the retaining bone, when failure occurs, it always involves bone trauma. This is due, in part, to too much fastener material embedded and too little retained bone.

By contrast, the present invention maximizes the bone being engaged while minimizing the fastener's thread, something impossible to do with a buttress thread and other common threads utilizing common manufacturing processes. The result is less bone trauma and less bone removed to increase bone strength to retain the fastener better.

This invention discards conventional thinking and manufacturing processes in the pursuit of new and desirable functions that can be achieved from the thread profile.

Heretofore manufacturers have adopted a simple and very fast manufacturing process that produce screws that function no better than common wood screws.

This invention (with, inter alia, its improved cutting edges, chip shard removal, reduced tooth width, a negligible thread angle, improved force distribution along thread facets and less bone removed) produces new interface characteristics with the bone while providing the surgeon with the best possible feel during the initial threading and torquing sequence.

The facets on the fastener's flanks may also include means to resist the osseous bone adjacent thereto from heaving parallel to the facets in response to loading. With a thread angle of 0 degrees, the primary redirecting force vector is caused by reaction to the larger helix angle. The facet's resistance to loads parallel to the facets is therefore in shear and resistance may be enhanced by a series of serrations imposed on the facets.

Preferably these serrations are configured as a series of tooth like projections and indentations running either spirally or concentrically on the facet face. Cancellous bone is resiliently elastic, which varies as to location and patient age. During installation, cancellous bone is compressed somewhat, and upon decompression after installation, pushes into the serrations, becoming embedded there within to resist shear forces when cancellous tissue heaves under load. The component of imposed forces parallel to the facets surface meets with the resistance caused by the serrations.

The cutters of the present invention are also provided with a second, active cutting site, distinct from the cutting site already mentioned. Frequently these screws need to be removed and in some cases are very difficult to extract due to subsequent bone development. The second cutting site is active only in removal and excises bone formed around the screw.

OBJECTS OF THE INVENTION

It is an object of the present invention to provide an improved cancellous screw fastener.

Another object is to provide greater feel for the surgeon by lowering insertion torque and reducing resistance to installation thereby providing lower friction and rapid insertion.

Another object is to provide a fastener which lends itself to mass production techniques.

A further object is to provide a fastener which exhibits enhanced holding in cancellous bone and minimizes bone trauma.

A further object is to increase the volume of bone which receives the fastener.

Viewed from a first vantage point, it is an object to provide: a fastener having threads with upper and lower flanks which are substantially parallel to each other, thereby, inter alia, minimizing anchoring bone displacement.

Viewed from another vantage point, it is an object of the present invention to provide a cancellous fastener with dual start threads.

Viewed from a further vantage point, it is an object to provide a fastener with at least two thread flights, each with a different crest diameter.

Another object of the present invention is to form a profile in bone which appears in section as a square wave crenellation.

Viewed from yet a further vantage point, it Is an object of the present invention to provide a fastener with an improved lead angle and thread flight which, in conjunction with previously enumerated object, induces beneficial force distribution under load.

Viewed from a further vantage point, it is an object of the present invention to provide a fastener with a plurality of self-tapping cutters which advance cut bone shards into an integrally formed through and away from threads of the fastener.

Viewed from another vantage point, it is an object of the present invention to provide a fastener with a thread angle of substantially zero.

Viewed from a further vantage point, it is an object of the present invention to provide a threaded fastener whose flank facets are substantially parallel to each other.

Viewed from a further vantage point, it is an object of the present invention to provide a fastener wherein the root diameter of a threaded portion is substantially equal to a diameter of an unthreaded shaft portion.

Viewed from a further vantage point it is an object of the present invention to provide a helix angle greater than that of a single start threaded fastener.

Viewed from another vantage point, it is an object of the present invention to provide a cutter which facilitates fastener removal as well as installation.

Viewed from another vantage point, it is an object of the present invention to provide resistance from heaving of the cancellous bone under load by increasing the surface area between the bone and thread facets. One way to increase the surface area and increase resistance to heaving and resultant shear is alter the surface of the facets.

DESCRIPTION OF PREFERRED EMBODIMENTS

Referring to the drawings, where like numerals reflect like parts, reference numeral 10 is directed to the fastener (screw) of the present invention. The screw 10 has an elongate shaft 13, substantially cylindrical along its length with a linear long axis 100 at its center. The screw may have a head 6 provided with a drive face 5 on its top surface. The face 5 can be contoured to accommodate a drive socket, screw driver tip, "torx" fitting, allen wrench, etc. to advance the screw.

Figure 7:
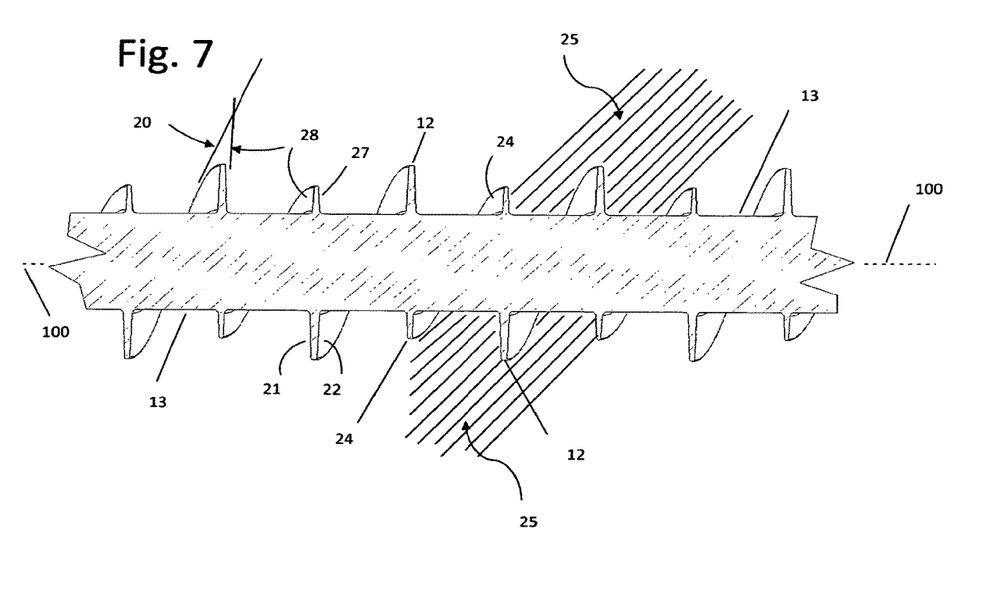
FIG. 7 is a sectional view of the faster, taken along its longitudinal axis.

A plurality of thread flights is contemplated, and the drawings illustrate a two flight embodiment. A first flight having a first thread 12 displays a greater crest diameter than a second flight having a second thread 24. Preferably these two flights are spaced from each other by 180 degrees and enjoy the same pitch. Accordingly, FIG. 7 shows that in section, a first major crest thread 12 always is diametrically opposed by a second minor crest thread 24 all along the thread paths. Bone "teeth" (cancellous bone) has been preserved between threads.

Unlike retained bone from a buttress thread (which merely comprises a "V" shape of constant dimension all along the fastener from the root diameter to the crest), the bone teeth 25 retained in the present invention evokes a saw tooth or crenelated appearance. Importantly the high and low areas of the bone teeth are also 180 degrees opposed all along the thread pattern, so that an area of minimal bone volume on one aspect is diametrically fortified by its corresponding maximal bone volume 180 degrees opposite.

When confronted with loads on the fastener, the opposing bone teeth and major/minor crest threads act in concert to oppose the loads and dissipate the loads into harmless (manageable) vectors through the cancellous bone. In fact, the loads imposed assist in circulating blood through the cancellous bone.

Because of the dual start thread structure, the helix angle 20 (FIG. 7) for a double start thread such as this is greater than a single start thread by an appreciable amount (typically just less than a factor of 2). This helix angle ordains the slope (or ramp) that the threads 12, 24 spiral about shaft 13. For example, a single start thread may have a helix angle of 11 degrees while the present invention's dual start helix angle 20 would be 21 degrees (from "horizontal" i.e. transverse to the long axis 100). Similarly, loads confronted by the fastener also see this greater helix angle and are dissipated into harmless vectors into the greater volume of cancellous bone (than would be the case in the prior art).

Each thread is formed as flanks having upper facets (nearer the proximal end adjacent head 6) and opposing lower facets. Thread 12 has upper facet 21 and lower facet 22; thread 24 has upper facet 28 and lower facet 27. FIG. 7 reveals that the facet pairs (21, 22) and (27, 28) enjoy substantial parallelism. That is facets 21,22,27,28 are all parallel to each other and substantially perpendicular to the long axis 100. This structure is especially adept at diffusing loads parallel to the long axis 100 and the threads' crest diameters are well suited to loads parallel but axially offset from the centerline long axis 100, primarily due to the greater volume of retained cancellous bone and its interplay with the varying crest diameters. As shown, thread 12 enjoys a greater crest diameter than thread 24.

Torsional loads and other loads not parallel to the long axis are countered by: the increased volume of cancellous bone's serpentine meandering about the fastener, the larger helix angle of the thread patterns, and the space between adjacent flanks. Notice shaft 13 is interposed between flanks. The cancellous bone does not see a "V" at the juncture of facets (as in the buttress thread) but rather a smooth expanse of cylindrical shaft 13. Thus, there are no "V-shape" pressure points at that site but instead a smooth area of tangential registry between bone and screw.

Because the flank facets are parallel to each other, the thread angle (the angle formed by the extension of adjacent upper and lower facets) is zero. Thus there are also no pressure points (additive vectors) on the cancellous bone caused by that angle.

Figure 6:
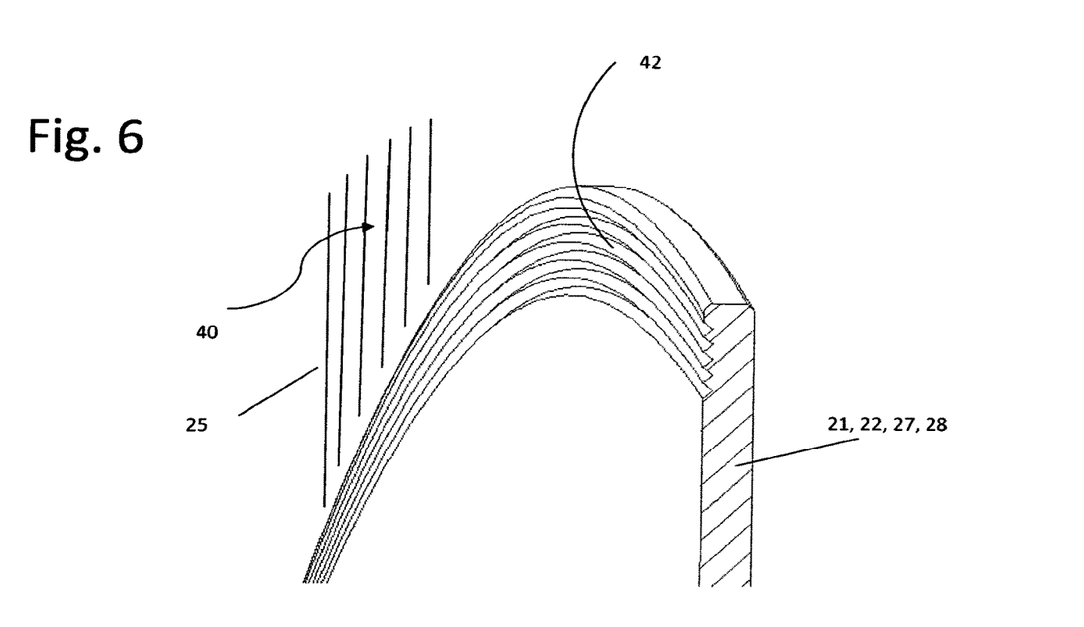
FIG. 6 is a perspective view of serration-like "V" shaped grooves on the facets to resist shear.

With a zero thread angle and parallel facets, loads transferred between cancellous bone and the flanks' facets are in shear; that is parallel to their interface. Resistance to shear loading can be enhanced by texturing the flanks, one example of which is shown in FIG. 6. Serrations 40, embodied here as a series of "V" shaped grooves 42, are embedded into one or more facets 21, 22, 27 and 28. The grooves receive the cancellous bone 25 there within.

As mentioned above, cancellous bone is amenable to both compression and expansion. During installation, the bone is slightly compressed, after which it expands and fills the grooves 42. Shear loads (parallel to the facet surface) are opposed by the increased friction caused by this structure. The grooves 42 may form a spiral, may be concentric or may instead appear only as a textured, knurled or matted surface. Thus, heaving of the cancellous bone is opposed by this increased friction.

Figure 1:
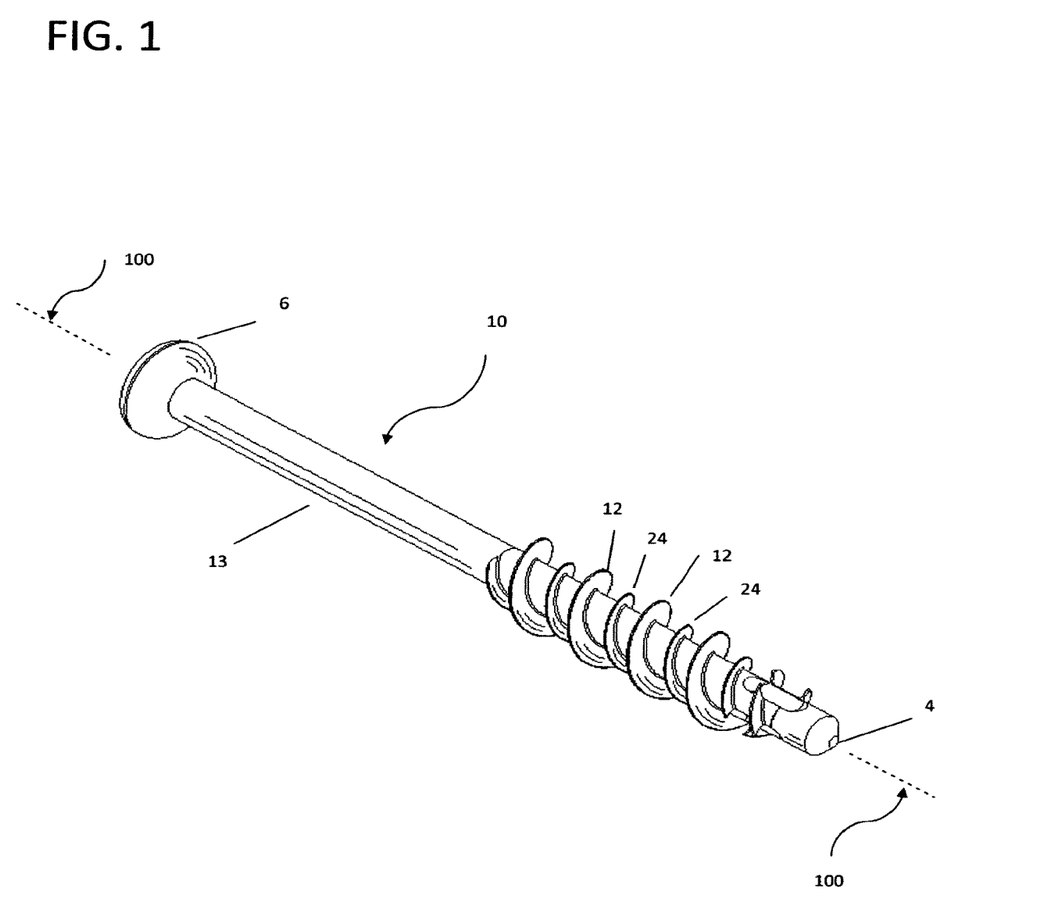
FIG. 1 is a perspective view of a fastener along a side thereof according to the present invention.
Figure 2:
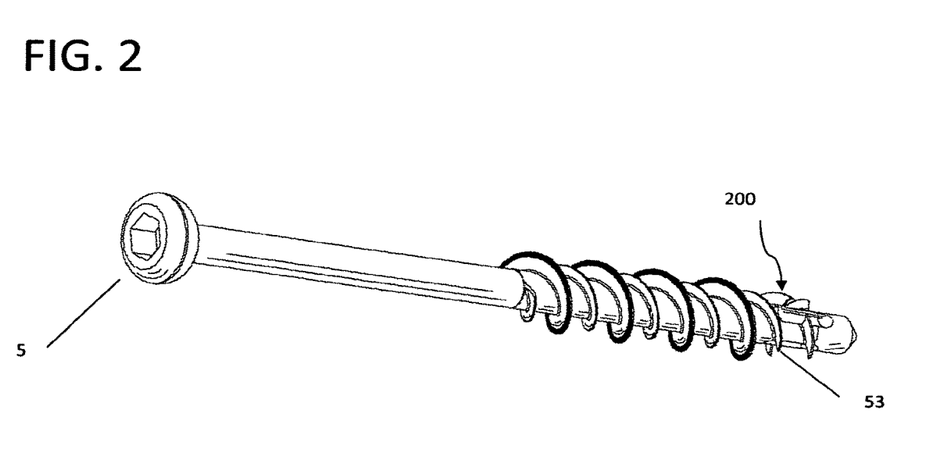
FIG. 2 is another perspective view, detailing the top, proximal end.
Figure 3:
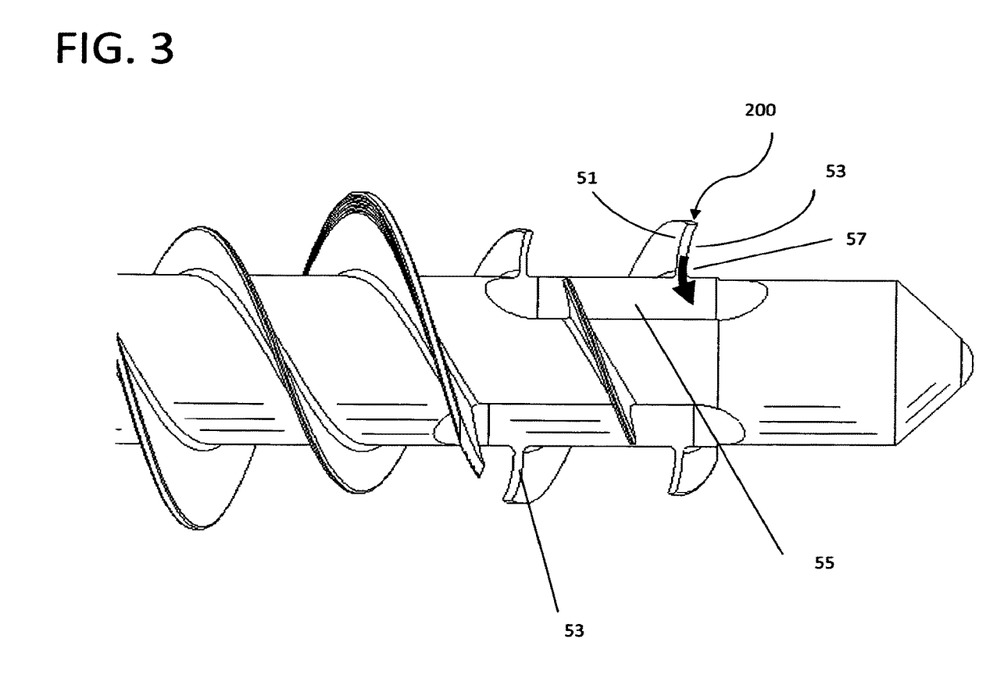
FIG. 3 is another perspective view, detailing the bottom, distal end.
Figure 4:
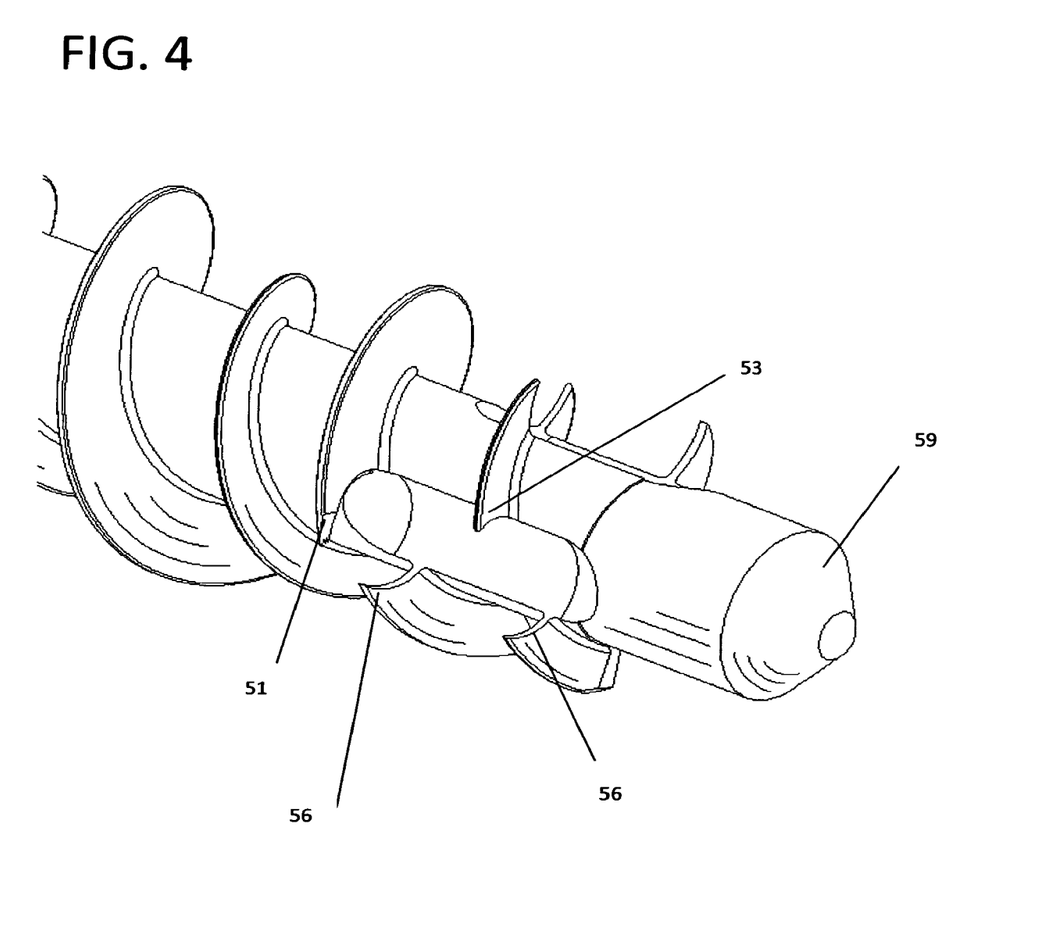
FIG. 4 is another perspective view of a distal end of the fastener, detailing the starting threads, centering pilot and self-tapping cutter structure.
Figure 5:
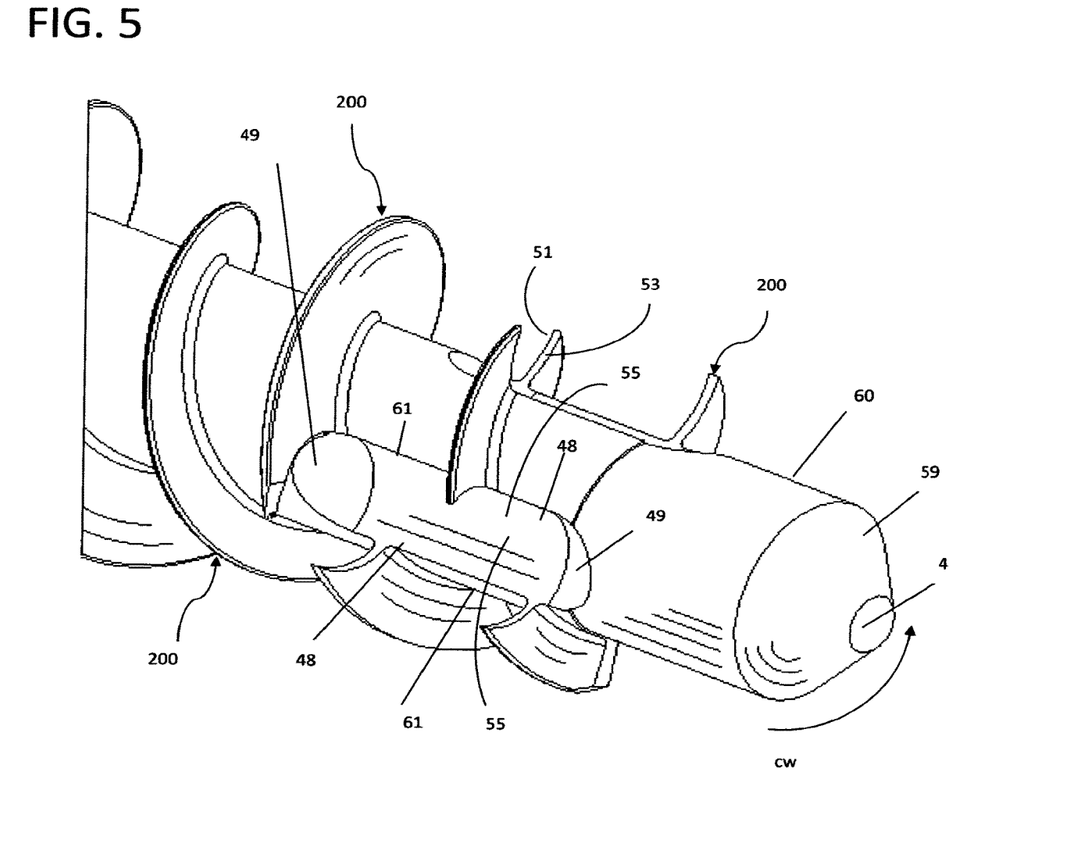
FIG. 5 is a differing perspective of FIGS. 3 and 4.

FIGS. 4 and 5 show pilot 59, cutters 200 and the concave bone shard retention trough 55 that substantially parallels the long axis 100 of screw 10 on an outer, annular surface of the cylindrical shaft 13. Pilot 59 features a conical tip which angularly transitions to the cylindrical shaft 13, resulting in a radial lead 60. Primary bone cutters 200 start on the "left-hand" side of troughs 55. That means that when the fastener advances into the bone (by tradition via "clockwise" or "right-handed" rotation), the active surface of the cutters 200 remove bone. Each cutter 200 has an active helical surface only a short distance (1 or more threads) towards the proximal end of the screw.

The actual cutting of bone shards by cutter 200 is caused by sharp leading cutting edges 53 formed at the base of the cutter 200 and has slightly blunted trailing cutting edges 51. A concave trough 55 placed near cutter 200 thus receives shards from the sharp leading cutting edge 53 which are severed by the blunted trailing edges 51. The troughs 55 are each strategically placed at the base of the cutters. The troughs 55 appear as very shallow, elongate ovals, having curved end walls 49 where the trough 55 tapers up to the shaft 13 and parallel, linear side walls 48 between which the trough 55 has its greatest depth.

The dimensions of the trough are designed to receive only a thin layer of bone shards there within. This allows uncut adjacent cancellous bone an opportunity to absorb the shards and minimizes the likelihood that a thick deposition of shards are present which, otherwise, may support necrosis by being deprived of blood circulation. Sharp edges 53 and blunted edges 51 combine to approximate a talon-like contour. Shards curl from the cutting edges and transition into the trough 55 along path 57.

FIG. 4 includes at least one sharp cutting surface 56 (on an opposite end of cutter 200) which is effective only when fastener rotation is for removing the fastener, in the present example counterclockwise. Historically, fasteners are occasionally troublesome to remove where the site has enjoyed active, restorative bone growth, and this cutter 56 facilitates easier fastener removal.

It is preferred that three cutters 200 be employed in forming the bone teeth 25 by removing bone shards and placing them into troughs 55. The cutter nearest the distal end is the first contributor in forming all threads 12, while the other, following cutters closer to the proximal end cooperate to remove additional shards providing clearance for minor diameter threads 24 and finally major diameter threads 12.

These features combine to cut clean threads and move the chips along chip path 57 pushing them into an adjacent trough 55 and out of the path of the advancing screw as it is helically turned into the bone. The leading edges 61 of the trough 55 at shaft (root) 13 are sharp and produce a precision fit within an inside diameter of a predrilled pilot hole by providing a positive scraping action as screw 10 turns inside the predrilled pilot hole. This scraping action forces the shards down into the troughs 55. The benefit here is that the cutting edges 51, 53 cause the shards to curl forward and follow the contour of trough 55 forward, and along path 57 away from the path of the advancing threads.

Stated alternatively, as the fastener is inserted clockwise CW, the leading cutting edges 53 progressively shave thin ribbons of bone which are then severed by trailing edge 51, advancing the shards forward and pushed by the cutter 200 over the scraping leading edge 61 of trough 55 in the direction 57. This creates a true self-tapping screw and also prevents the chips from being drawn into the advancing screw threads and the bone. This results in much lower cutting pressure, cleaner threads and less damage to the bone. (If the chips can't get out of the way they get drawn into the path of the threads and get crushed into the surrounding bone. If this happens, the trapped shards can initiate an inflammation process resulting in the immune system attacking these shard chips as foreign bodies with eventual absorption, causing voids next to the threads eventually resulting in loosening of the screw threads 12 and 24.)

The pilot 59 has a substantially rounded, radiused distal end 4 shown in the drawings. The conical transition of pilot 59 includes a lead 60 to shaft 13. A pilot 59 provides a transition between the radiused distal end 4 and the cylindrical shaft 13 via cylindrical lead section 60. This radiused end 4, angular transition 59 and lead 60 force the fastener 10 to remain in the predrilled pilot hole and helps find the pilot hole as it passes through an opposite side wall or portion of bone, thereby assuring registry of the fastener 10 through all subsequent pilot drilled portions of bone assuring maximum purchase and pull out strength.

In use, preferably a pilot hole is predrilled and the fastener 10 is oriented there over. The angular transition 59, radiused end and cylindrical lead 60 of the pilot 59 nest within the predrilled pilot hole. Advancement of the fastener by clockwise rotation (CW) causes the leading (left handed) cutting edges 53 to incrementally shave bone shards away from the fastener, with trailing edge 51 pushing the shards downward along path 57 into the trough 55 concavity after having been chipped off by the trailing cutting edges 53 and assisted by edges 61 on the periphery of the trough 55. Bone is thus threaded in conformance with the fastener's tooth profile resulting in bone teeth 25. As the fastener 10 advances into the bone, the bone teeth 25 provide positive engagement with the fastener 10 without perceptible friction (deleterious heat buildup) or unwanted radial forces experienced by the surgeon who—unlike the prior art—can advance the fastener with very little effort.

This gives the surgeon precise information on the progress of the procedure. The lead 60 on the pilot tracks the predrilled hole precisely without deleterious wandering and trauma to the adjacent bone.

This contact induces a change in force which is perceptible to the surgeon unlike the prior art. The surgeon thus has better "feel" to sense and adjust the compression/torque most beneficial to the procedure. Incidentally, the same improved tactile feedback exists where the fastener does not have a head, but instead is to be countersunk.

Having described an illustrative form of the invention and having been thus informed, it should be apparent that modifications are contemplated as being part of the invention as proscribed by the appended claims.

I claim:

1. A medical fastener, comprising:
an elongate shaft having a proximal end and a distal end,
a first thread helically wound around said shaft, said first thread having facets defining surfaces as upper and lower flanks, said upper and lower flanks oriented in substantially parallel relationship,
a self-tapping cutter having a cutting element extending outwardly from a surface of the elongate shaft and defining a sharp leading edge and an adjacent blunted trailing edge with respect to advancement of the first thread upon rotation thereof, the sharp leading edge and the blunted trailing edge cooperating to form a talon shaped cross-section of the cutting element, and a trough operatively communicating therewith to receive bone shards therein.

2. The fastener of claim 1, further comprising a second thread helically wound around said shaft, said second thread having facets oriented substantially diametrically opposite from said first thread facets.

3. The fastener of claim 2, wherein said second thread facets are substantially parallel to each other, and said first thread has a crest diameter greater than said second thread crest diameter.

4. The fastener of claim 2, wherein the thread flanks of the first thread and the thread flanks of the second thread are oriented at a right angle relative to said elongate shaft, whereby the thread flanks of the first thread and the thread flanks of the second thread are configured to form a series of square-wave teeth profile within a bone.

5. The fastener of claim 2, further comprising a second self-tapping cutter disposed on a distal end of said second thread.

6. The fastener of claim 5, further comprising a third self-tapping cutter located on a distal end of one of said threads.

7. The fastener of claim 1, further comprising a self-tapping first cutter on said distal end to remove bone shards during fastener installation.

8. The fastener of claim 7, wherein said first self-tapping cutter supports a removal cutter to excise bone during fastener removal.

9. The fastener of claim 1, wherein said facets include means to resist shear forces imposed on cancellous bone adjacent thereto.

10. The fastener of claim 9, wherein said means to resist shear forces is embodied as serrations disposed on at least one said facet.

11. The fastener of claim 1, having a thread angle of substantially zero.

12. The fastener of claim 1, further comprising a pilot on said distal end.

\* \* \* \* \*